(12) United States Patent
Huang et al.

(10) Patent No.: US 8,663,972 B2
(45) Date of Patent: Mar. 4, 2014

(54) RHIZOPUS ORYZAE STRAIN, MUTAGENESIS AND SCREENING METHODS THEREOF, AND METHODS OF FERMENTING TO PRODUCE FUMARIC ACID

(76) Inventors: He Huang, Jiangsu (CN); Shuang Li, Jiangsu (CN); Qing Xu, Jiangsu (CN); Zhen Gao, Jiangsu (CN)

( * ) Notice: Subject to any disclaimer, the term of this patent is extended or adjusted under 35 U.S.C. 154(b) by 0 days.

(21) Appl. No.: 13/992,233

(22) PCT Filed: Apr. 16, 2011

(86) PCT No.: PCT/CN2011/072903
§ 371 (c)(1),
(2), (4) Date: Jun. 6, 2013

(87) PCT Pub. No.: WO2012/126187
PCT Pub. Date: Sep. 27, 2012

(65) Prior Publication Data
US 2014/0004560 A1 Jan. 2, 2014

(30) Foreign Application Priority Data
Mar. 24, 2011 (CN) .......................... 2011 1 0072287

(51) Int. Cl.
C12N 1/14 (2006.01)
C12N 15/01 (2006.01)
C12P 7/46 (2006.01)
C12P 19/20 (2006.01)

(52) U.S. Cl.
USPC ........... 435/256.6; 435/446; 435/145; 435/96

(58) Field of Classification Search
USPC ................................ 435/256.6, 446, 145, 96
See application file for complete search history.

Primary Examiner — Rosanne Kosson
(74) Attorney, Agent, or Firm — George G. Wang; Bei & Ocean

(57) ABSTRACT

A *rhizopus oryzae* strain, mutagenesis and screening methods thereof, and methods of producing fumaric acid by fermentation. The strain is named as *Rhizopus oryzae* ME-F13, and deposited in China Center for Type Culture Collection with depository number CCTCC M 2010351. The strain is obtained by physically mutagenizing the original strain ME-F12 through ion injection, culturing the processed bacteria on the solid selective plate containing 2-D-deoxylucose (2-DG) and picking up 2-DG-resistant single colony. The strain is capable of simultaneously saccharifying starchy material and fermenting it to produce fumaric acid. With an improved enzymatic activity, the strain can be directly used to ferment raw starchy materials without needing pre-saccharifying.

12 Claims, 1 Drawing Sheet

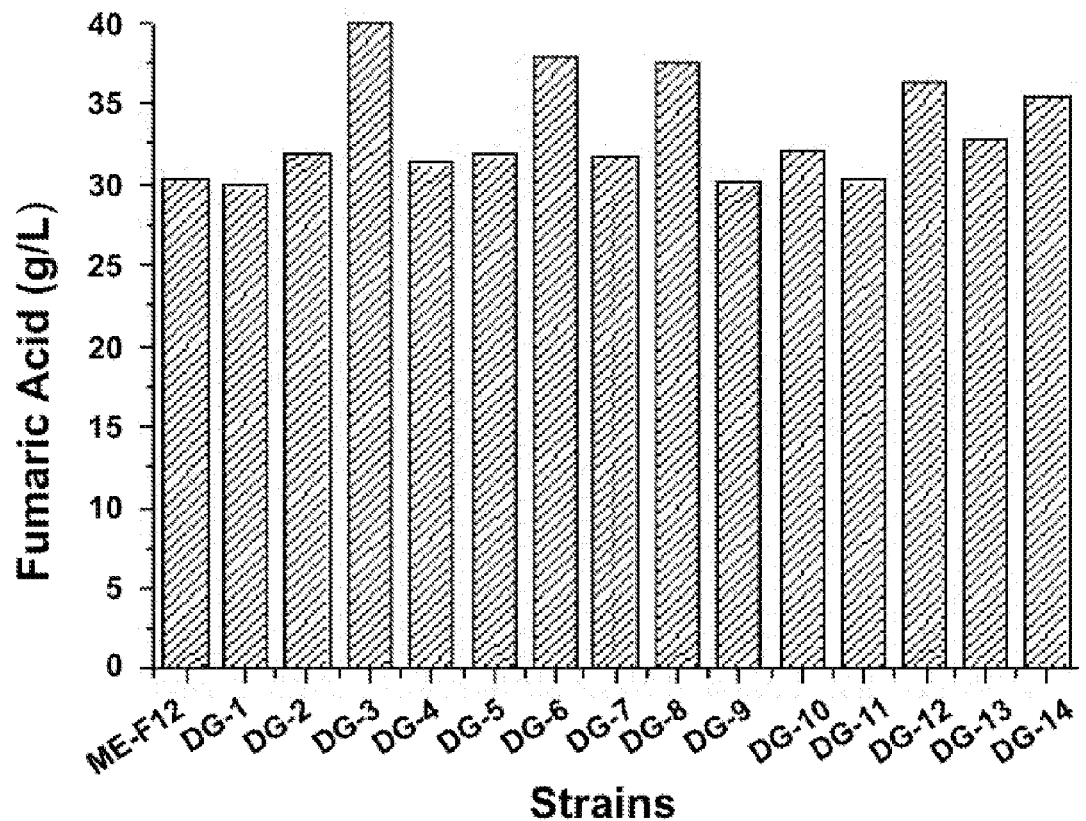

RHIZOPUS ORYZAE STRAIN, MUTAGENESIS AND SCREENING METHODS THEREOF, AND METHODS OF FERMENTING TO PRODUCE FUMARIC ACID

FIELD OF THE INVENTION

The present invention, in the field of bioengineering technology, relates to a *rhizopus oryzae* strain, the mutagenesis and screening methods thereof, and the method of producing fumaric acid by fermentation. Specifically, it relates to a mutant strain that can produce fumaric acid from starch materials through simultaneous saccharification and fermentation (SSF), the mutagenesis and screening methods to obtain this strain and the methods to produce fumaric acid using this strain with starch as raw material.

BACKGROUND OF THE INVENTION

Fumaric acid is an important basic organic chemical raw material and bulk chemical product widely used in the areas of coating material, resin, pharmaceutical material, plasticizer and food additive, etc, having important commercial values. Fumaric acid can also be used as raw material for further synthesizing a number of high-value derivatives, such as DMF and ferrous fumarate. Furthermore, as an important four-carbon platform compound, fumaric acid may be used as a base material for the synthesis of various four-carbon compounds, such as L-aspartic acid, malic acid, succinic acid, maleic acid, 1,4-butanediol, Y-butyrolactone and tetrahydrofuran, via enzyme catalytic conversion, esterification and hydrogenation.

At present, commercial fumaric acid is mostly produced by chemical methods, such as the catalytic oxidation of benzene or butane to produce maleic acid or maleic anhydride, and then to obtain fumaric acid by isomerization. However, it is now facing the main difficulties due to the shortage of fossil resources, increase in production cost and pollution to the environment. The oil crisis in the 1970s forced people to make more efforts in the research of producing fumaric acid through microbial fermentation, and mycete, yeast and bacteria have been used for fermentation. Among them, *Rhizopus* became the focus of research for its features of simple culture requirements, high adaptation to environments and fast growing, and the family includes *rhizopus oryzae, rhizopus arrhizus* and *rhizopus nigricans*. *Rhizopus oryzae*, as one of the best strains for producing fumaric acid, has attracted an extensive attention.

However, commercial production of fumaric acid with fermentation methods has not been realized because of high raw material cost, which accounts for the most in the total production cost, and cutting the raw material cost has become the key for microbiol production of fumaric acid (Gangl I C, Weigang W A, Keller F A. Appl Microbiol Biotechnol, 1990, 24-25(1): 663-667), but the fumaric acid yield is quite low by using traditional processes with cheap starch as raw material (Moresi M, Parente E, Petruccioli M, Federici F J. Chem Tech Biotechnol, 1992, 54(3): 283-290; Carta F S, Soccol C R, Ramos 25 LP, Fontana J D. Bioresour Technol, 1999, 68(1): 23-28). Therefore, improving strains by widening the substrate spectrum has become the primary task. Researches show that, 2-Deoxyglucose (2-DG) is a glucose analog that can cause severe catabolite repression when strains synthesize hydrolase (glucoamylase, cellulase, xylanase and glucosidase), therefore it is often used to screen for mutants with high glucoamylase activity resisting to catabolite repression (Ghosh A, Chatterjee B, Das A Biotechnol Lett, 1991, 13(7): 515-520; Sarangbin S, Kirimura K, Usami S, Appl Microbiol Biotechnol, 1993(2-3), 40: 206-210; Chandra M, Kalra A, Sangwan N S, Gaurav S S, Darokar P M, Sangwan S R. Bioresour Technol, 2009, 100(4): 1659-1662). If the glucoamylase activity of *Rhizopus oryzae* can be increased, fumaric acid can be produced by simultaneously saccharifying starchy material and fermenting it without the need to saccharify the raw material first.

SUMMARY OF THE INVENTIONS

One object of this invention is to provide a *Rhizopus oryzae* that can be used to produce fumaric acid by simultaneously saccharifying starchy material and fermenting it.

Another object of this invention is to provide a method for the mutagenesis and screening of the *Rhizopus oryzae*.

Another object of this invention is to provide the methods to produce fumaric acid with a *Rhizopus oryzae* strain.

These objects of the invention are realized with the following technical plans:

I. A *Rhizopus oryzae* strain, classified and named as *Rhizopus oryzae* ME-F13 and deposited in the China Center for Type Culture Collection on Dec. 16, 2010, located at Wuhan University, Wuhan 430072, China, with the depositary number CCTCC No.: M 2010351, was used to produce fumaric acid by performing simultaneously a saccharifying process and fermentation of starchy material as the carbon source. This biological deposit was made in accordance with the Budapest Treaty.

II. The mutagenesis and screening method for obtaining the *Rhizopus oryzae* ME-F13 of the invention were characterized by the following steps:

1) The original strain of *Rhizopus oryzae* ME-F12 (ME-UN-8) was mutagenized by nitrogen ion implantation, to obtain the mutant strain.

2) The spore suspension of the mutant obtained in step 1) was coated onto a selective solid culture medium plate containing 2-DG for cultivation, to obtain the strains with 2-DG resistance.

3) The genetic stability of the 2-DG resisting mutants obtained in step 2) was investigated: Growing single colonies were transferred into a fermentation medium in a shake flask with starch as the carbon source. After fermentation, the mutant with the highest increase of glucoamylase activity and fumaric acid yield over its parent strain was finally selected, and named as *Rhizopus oryzae* ME-F13.

The ion injection physical mutagenesis method described in step 1) is performed with $N^+$ beam at energy of 15 KeV, with a dose of $50 \times 10^{13}$ to $300 \times 10^{13}/cm^2$, and the operation pressure in the target chamber was approximately $10^{-3}$ Pa.

The solid selective culture medium used in step 2) contained 0.2 g/L to 0.6 g/L 2-DG.

The carbon source in the solid selective culture medium containing 2-DG used in step 3) is glycerol, with a concentration of 30 g/L, and the other nutrient components are: 2 g/L urea, 0.6 g/L $KH_2PO_4$, 0.5 g/L $MgSO_4 \cdot 7H_2O$, 0.11 g/L $ZnSO_4$, 0.88 g/L $FeSO_4 \cdot 7H_2O$, and 20 g/L agar.

III. Fumaric acid production from starch materials through SSF using *Rhizopus oryzae* ME-F13 according to the present invention was carried out as follows: the spore suspension of ME-F13 was inoculated in a flask for making the seed culture and the seed culture was then inoculated into the fermentation medium for producing fumaric acid through SSF, using the glucoamylase produced by itself, wherein in the seed and fermentation media, the carbon source was dextrin liquefied from starchy materials.

Specifically, spore suspension was prepared by washing off spores with sterilized water from *Rhizopus oryzae* ME-F13 cultured on slants for 6-7 days, and then the spore suspension was inoculated into a flask with the seed medium and cultured at 30 to 40 and pH 2.5 to 2.7 for 28 to 32 hours. The seed culture was inoculated at an amount of 5%—10% (v/v) into a flask with the fermentation medium and cultured at 30 to 40 for 60-85 hours. The seed and fermentation media were prepared by mixing the liquefied starchy materials and common inorganic salt, which were respectively autoclaved at 115 to 121 for 20 min. The ingredients were mixed after cooling, and $CaCO_3$ was added into the fermentation medium as a neutralizer.

The method to prepare liquefied starchy materials: starchy materials were mixed in distilled water at 8% to 12% (w/v) concentration, the suspension was heated to 70 and then added with thermostable-amylase (at 800 U/g to 1000 U/g dry substrate bases). The resulting mixture was kept at this temperature for 10 min and then heated to 90, and the amount of residual starch was measured by the color reaction of iodine. When the blue coloration stays unchanged in the iodine test, the mixture was heated to 100 and boiled for 5-10 min. The liquefied materials were filtered with two layers of gauze. After cooling, the filtrate was diluted to the required substrate concentration for fermentation.

The beneficial effects of the present invention are described as follows:

In this invention, the *Rhizopus oryzae* ME-F12 (ME-UN-8) capable of producing fumaric acid was used as the original strain, and the above-mentioned method was used to select and obtain the mutant *Rhizopus oryzae* ME-F13 which can be used to produce fumaric acid through SSF from starchy materials. This mutant features a significantly increased glucoamylase activity, about 2.5 times that of the original strain, and therefore it can be used to produce fumaric acid with starchy materials through the SSF process without adding commodity glucoamylase. This simultaneous saccharifying and fermentation process, with liquefied starchy materials as substrate and using the glucoamylase produced by itself, not only has the advantages of the simultaneous saccharifying process, such as relief of the high concentration substrate inhibition, shorter fermentation time and lower equipment cost, but also has solved the problem of conflicting conditions for glucoamylase activity and fermentation (temperature and pH) in simultaneous saccharifying, thus offering outstanding prospects for industrial applications.

BRIEF DESCRIPTION OF THE DRAWINGS

FIG. 1 shows a comparison of fumaric acid yields by selected strains.

DETAILED DESCRIPTION OF PARTICULAR EMBODIMENTS OF THE INVENTION

General Description:

The method to prepare liquefied starchy materials as described in this invention: starchy materials were mixed with distilled water at 8% to 12% (w/v) concentration, the suspension was heated to 70 and then added with thermostable-amylase at 800 U/g dry substrate bases. The resulting mixture was kept at this temperature for 10 min and then heated to 90, and the residual starch was measured by the color reaction of iodine. When the blue coloration stays unchanged in the iodine test, the mixture was heated to 100 and boiled for 5-10 min. The liquefied materials were filtered with two layers of gauze. After cooling, the filtrate was diluted to the required substrate concentration for fermentation.

Bromocresol green agar medium was composed of 0.2 g/L bromocresol green, 1.0 g/L sodium deoxycholate, 80 g/L soluble starch, 1 g/L urea, 0.6 g/L $KH_2PO_4$, 0.5 g/L $MgSO_4.7H_2O$, 0.11 g/L $ZnSO_4$, 0.088 g/L $FeSO_4.7H_2O$, and 20 g/L agar.

Solid selective 2-DG/glycerol agar medium was composed of 0.2 g/L 2-DG, 30 g/L glycerol, 2 g/L urea, 0.6 g/L $KH_2PO_4$, 0.5 g/L $MgSO_4.7H_2O$, 0.11 g/L $ZnSO_4$, 0.088 g/L $FeSO_4.7H_2O$, and 20 g/L agar.

Solid selective 2-DG/glucose agar medium was composed of 0.6 g/L 2-DG, 30 g/L glucose, 2 g/L urea, 0.6 g/L $KH_2PO_4$, 0.5 g/L $MgSO_4.7H_2O$, 0.11 g/L $ZnSO_4$, 0.088 g/L $FeSO_4.7H_2O$, and 20 g/L agar.

Seed medium 1 was composed of 30 g/L soluble starch, 2 g/L urea, 0.6 g/L $KH_2PO_4$, 0.5 g/L $MgSO_4.7H_2O$, 0.11 g/L $ZnSO_4$, and 0.088 g/L $FeSO_4.7H_2O$ at pH 2.5 to 2.7.

Seed medium 2 was composed of 30 g/L corn power, degermed corn powder or cassava powder at pH 2.5 to 2.7.

Fermentation medium 1 was composed of 80 g/L soluble starch, 0.1 g/L urea, 0.6 g/L $KH_2PO_4$, 0.5 g/L $MgSO_4.7H_2O$, 0.11 g/L $ZnSO_4$, 0.088 g/L $FeSO_4.7H_2O$, and 40 g/L $CaCO_3$.

Fermentation medium 2 was composed of 80-120 g/L corn power, degermed corn powder or cassava powder, and 40-60 g/L $CaCO_3$.

Fumaric acid was measured by high-performance liquid chromatography (DIONEX Summit P680). The chromatography column was Aminex HPX-87 H (Bio-Rad, USA) under the following conditions: column temperature, 65; UV absorption band 210 nm; mobile phase, 0.005 mmol/L H2SO4; flow rate, 0.8 mL/min; and sample volume, 20 L.

Embodiment 1

Mutagenesis Treatment of *Rhizopus oryzae* by Ion Injection

Take a slant (PDA solid medium) of *Rhizopus oryzae* ME-F12 (CCTCC NO: M 207023) having cultured for 5-6 days with dense and dark spores, wash off the spores with sterile water, and inoculate the suspension of spores in a sterilized triangle flask containing ice-filled glass beads. Afterward, the suspension was fully oscillated at 35 and 200 rpm for 30 min to ensure that all spores were dispersed homogeneously. Then, the spore suspension was filtered with sterilized degreased cotton, two layers of gauze or minor paper. The concentration of the spore suspension was determined directly with a hemacytometer and adjusted to $10^7$ spores/mL with sterile water. Approximately 0.1 mL of the above spore suspension was spread on a sterilized Petri dish to form a single-cell layer and dried at room temperature.

Then the dishes were put into $N^+$ beams injector for treatment at a dose of $50 \times 10^{13}$ to $300 \times 10^{13}/cm^2$ at 15 keV energy. The operation pressure in the target chamber was $10^{-3}$ Pa. Then the dishes were taken out, and eluted with 1 mL sterilized water, the spore concentration was adjusted to $10^6$ for use later.

Embodiment 2

Strain Selection

Initial screening: Approximately 100 μL of the spore suspension after treatment with ion injection mutagenesis was coated onto solid selective 2-DG/glycerol agar medium and cultured for 2-3 days.

Pick out the singular colonies surviving in the solid selective 2-DG/glycerol agar medium, and transfer them onto PDA slants with bromocresol green for a secondary screening. The fumaric acid produced during the growth of *Rhizopus oryzae* can form a yellow discoloring ring in the medium around the colony. The diameter ratio can be calculated by measuring the diameter of this ring and of the colony, and singular colonies with a larger diameter ratio were selected and transferred to the solid selective 2-DG/glucose medium. After five generations of culture, the stable strains keeping on growing and producing spores were transferred to the PDA slants for preservation and further selection.

Shake flask rescreening: 14 mutants resisting to 2-DG were selected after the initial and secondary screenings. A spore suspension was made from each of these mutants using the method described in Embodiment 1, and was inoculated at 2% on seed medium 1, transferred into a shaker at 220 rpm and cultured at 35 for 30 hours. The obtained seed was cultured at 10% (v/v) in fermentation medium 2, and put into a shaker at 220 rpm and cultured at 35 for 60-85 hours. After fermentation, the fumaric acid yield was determined, and the results are shown in FIG. 1. FIG. 1 demonstrates that 5 selected strains, respectively DG-3, DG-6, DG-8 DG-12, and DG-14, produced fumaric acid from soluble starch through SSF at a yield 10% higher than that of their parent strain.

Embodiment 3

Comparison of Fermentation Performance of Mutant and Parent Strains

From the mutant DG-3, which produced highest fumaric acid yield after 6-7 days of slant culture, the spore suspension was prepared by washing off the spores with sterilized water, and inoculated in seed medium 1, culturing at 35, 200 rpm and pH 2.5 for 30 hours. Then, the seed was inoculated into the fermentation medium at 10% (v/v), for culturing at 35 and 200 rpm for 85 hours. At the end of fermentation, the glucoamylase and fumaric acid yield were determined. The measurements were repeated three times, and the average results are shown in Table 1. The result shows that, under the identical fermentation conditions, after mutagenesis treatment and screening of *Rhizopus oryzae* ME-F12 (ME-UN-8), the glucoamylase activity of the obtained mutant DG-3 is 156% higher than that of its parent, with fumaric acid yield as high as 39.80 g/L, an increase of 28% from its parent.

TABLE 1

|  | Glucoamylase activity (U/mL) | Fumaric acid production (g/L) |
|---|---|---|
| *Rhizopus oryzae* ME-F12 | 7.24 | 31.04 |
| Mutant DG-3 | 18.60 | 39.80 |

The mutant strain DG-3 was named as *Rhizopus oryzae* ME-F13, and deposited in China Center for Type Culture Collection at Wuhan University, with a depository number CCTCC M 2010351.

Embodiment 4

Production of Fumaric Acid Using *Rhizopus oryzae* ME-F13 from Raw Starch Materials Through SSF A spore suspension was obtained from *Rhizopus oryzae* ME-F13 after 6 day slant culture by washing off spores with sterilized water. The suspension was inoculated to seed medium 2 and cultured at 35, 200 rpm and pH 2.5 for 30 hours, and then the seed was inoculated at 10% (v/v) into a 5 L bioreactor tank containing fermentation medium 2 under stiffing, and cultured at 35, 1 vvm ventilation ratio and 400 rpm for 85 hours, performing SSF with *Rhizopus oryzae* ME-F13 using several different raw starch materials such as, corn power, degermed corn powder, and cassava powder. The results are presented in Table 2.

TABLE 2

| Substrate | Substrate concentration (g/L) | Fumaric acid yield (g/L) | Conversion (g/g) | Productivity (g/L · h) |
|---|---|---|---|---|
| Corn power | 80 | 34 ± 1.0 | 0.45 | 0.40 |
|  | 100 | 45 ± 1.5 | 0.51 | 0.53 |
| Degermed corn powder | 120 | 52 ± 1.2 | 0.46 | 0.61 |
| Cassava powder | 120 | 47 ± 1.0 | 0.44 | 0.55 |

Embodiment 5

Production of Fumaric Acid Using *Rhizopus oryzae* ME-F13 from Raw Starch Materials Through SSF The similar fermentation method as in Embodiment 4 was used in this embodiment:

A spore suspension was prepared from *Rhizopus oryzae* ME-F13 after 7 day slant culture by washing off spores with sterilized water. The suspension was inoculated to seed medium 2 and cultured at 40, 200 rpm and pH 2.7 for 28 hours, and then the seed was inoculated at 8% (v/v) into the 5 L bioreactor tank containing fermentation medium 2 under stiffing, and cultured at 40, 1 vvm ventilation ratio and 400 rpm for 60 hours. The result is presented in Table 3.

TABLE 3

| Substrate | Substrate concentration (g/L) | Fumaric acid yield (g/L) | Conversion (g/g) | Productivity (g/L/h) |
|---|---|---|---|---|
| Corn power | 80 | 30 ± 1.0 | 0.41 | 0.50 |
|  | 100 | 39 ± 1.5 | 0.45 | 0.65 |
| Degermed corn powder | 120 | 45 ± 1.2 | 0.42 | 0.75 |
| Cassava powder | 120 | 43 ± 1.0 | 0.39 | 0.71 |

Embodiment 6

Production of Fumaric Acid Using *Rhizopus oryzae* ME-F13 from Raw Starch Materials Through SSF The similar fermentation method as in Embodiment 4 was used in this embodiment:

A spore suspension was prepared from *Rhizopus oryzae* ME-F13 after 7 day slant culture by washing off spores with sterilized water. The suspension was inoculated to seed medium 2 and cultured at 30, 200 rpm and pH 2.6 for 32 hours, then the seed was inoculated at 5% (v/v) into the 5 L bioreactor tank containing fermentation medium 2 under stiffing, and cultured at 30, 1 vvm ventilation ratio and 400 rpm for 72 hours, see Table 4 for the results.

TABLE 4

| Substrate | Substrate concentration (g/L) | Fumaric acid yield (g/l) | Conversion (g/g) | Productivity (g/L/h) |
|---|---|---|---|---|
| Corn power | 80 | 3 ± 1.0 | 0.46 | 0.45 |
|  | 100 | 44 ± 1.5 | 0.50 | 0.61 |
| Degermed corn powder | 120 | 50 ± 1.2 | 0.45 | 0.69 |
| Cassava powder | 120 | 45 ± 1.0 | 0.42 | 0.63 |

What is claimed is:

1. An isolated *Rhizopus oryzae* strain, with the classification and name *Rhizopus oryzae* ME-F13, deposited in the China Center for Type Culture Collection on Dec. 16, 2010 with the preservation number CCTCC No.: M 2010351.

2. A method of making the *R. oryzae* strain of claim 1, by mutating a *Rhizopus oryzae* strain and screening for glucoamylase production and fumaric acid production, comprising the following steps:
   a) obtaining the *R. oryzae* strain ME-UN-8 and mutating it by nitrogen ion implantation to yield mutant strains;
   b) obtaining spores from the mutant strains made in step (a);
   c) coating the spores obtained in step (b) onto a selective solid culture medium plate containing 2-deoxy-d-glucose (2-DG), to obtain strains with 2-DG resistance;
   d) culturing single colonies obtained from growth on the solid medium in step (c) in culture medium in shake flasks comprising starch as the carbon source;
   e) determining the level of glucoamylase activity of each flask culture and the amount of fumaric acid in each flask culture; and
   f) selecting the mutant having the highest increase of glucoamylase activity in its culture medium and of fumaric acid yield relative to the strain of step (a), wherein the selected mutant is named as *Rhizopus oryzae* ME-F13.

3. The method of claim 2, wherein the nitrogen ion implantation is N+ injection performed at an energy of 15 KeV and a dose of $50 \times 10^{13}$ to $300 \times 10^{13}/cm^2$, and the operation pressure in the target chamber is $10^{-3}$ Pa.

4. The method of claim 2, wherein the solid selective culture medium comprises 0.2 g/L to 0.6 g/L of 2-DG.

5. The method of claim 2, wherein the solid culture medium containing 2-DG comprises 30 g/L of glycerol, 2 g/L of urea, 0.6 g/L of $KH_2PO_4$, 0.5 g/L of $MgSO_4 \cdot 7H_2O$, 0.11 g/L of $ZnSO_4$, 0.88 g/L of $FeSO_4 \cdot 7H_2O$, and 20 g/L of agar.

6. A method of making fumaric acid, comprising the following steps:
   a) inoculating a seed medium with a suspension of spores of the *Rhizopus oryzae* ME-F13 strain of claim 1;
   b) culturing the inoculated seed medium;
   c) inoculating medium comprising starchy materials in a fermentation flask with the seed culture obtained in step (b), wherein the culture produces glucoamylase, wherein the glucoamylase hydrolyzes the starchy materials to make dextrin, and wherein the dextrin is a carbon source for the strain of step (a);
   d) culturing the inoculated medium in the flask, wherein the culture of the strain of step (a) produces fumaric acid; and
   e) isolating the fumaric acid made in step (d).

7. The method of claim 6, wherein the spore suspension is prepared by culturing the strain of claim 1 on agar slants for 6-7 days and washing off the resulting spores with sterile water.

8. The method of claim 6, wherein the inoculated seed medium is cultured at pH 2.5 to 2.7 for 28 h to 32 h.

9. The method of claim 6, wherein the seed culture of step (c) is inoculated into the flask in amount of 5-10% of the volume of the flask, and wherein the flask is cultured for 60 h to 85 h.

10. The method of claim 6, wherein the seed and fermentation media are prepared by mixing liquefied starchy materials and an inorganic salt, autoclaving the media at 115 to 121° C. for 20 minutes, mixing the media after cooling, and add $CaCO_3$ to fermentation medium to adjust the pH to a neutral pH.

11. The method of claim 10, wherein the seed and fermentation media are prepared by the following steps:
   a) mixing starchy materials with distilled water at a concentration of 8% to 12% (w/v) to make a suspension;
   b) heating the suspension to 70 degrees and then adding a thermostable amylase having an activity of 800 to 1000 U/g;
   c) incubating the mixture of step (b) for 10 minutes and then heating it to 90 degrees;
   d) measuring the amount of residual starch by a color reaction with iodine, wherein, when the blue coloration stays unchanged in the iodine test, the mixture is heated to 100 degrees and boiled for 5-10 minutes;
   e) filtering the liquid obtained in step (d) through two layers of gauze and cooling the filtrate; and
   f) diluting the filtrate to a concentration that can be used in fermentation.

12. The method of claim 6, wherein the starchy materials are selected from the group consisting of soluble starch, corn powder, degermed corn powder and cassava powder.

* * * * *